United States Patent [19]
Imbert et al.

[11] Patent Number: 5,607,466
[45] Date of Patent: Mar. 4, 1997

[54] CATHETER WITH A STENT

[75] Inventors: Christian Imbert, Versoix; Eugen Hofmann, Zurich; Marc Gianotti, Wiesendangen, all of Switzerland

[73] Assignee: Schneider (Europe) A.G., Bulach, Switzerland

[21] Appl. No.: 433,281

[22] Filed: Apr. 28, 1995

Related U.S. Application Data

[63] Continuation of Ser. No. 10,102, Jan. 28, 1993, abandoned.

[30] Foreign Application Priority Data

Feb. 3, 1992 [EP] European Pat. Off. ............ 92200294

[51] Int. Cl.$^6$ .......................... A61F 2/06; A61M 29/00; A61M 5/178
[52] U.S. Cl. ........................ 623/1; 606/194; 604/197
[58] Field of Search .................... 623/1, 11, 12; 606/191–200; 600/36; 604/167, 96

[56] References Cited

U.S. PATENT DOCUMENTS

| | | |
|---|---|---|
| 4,572,186 | 2/1986 | Gould et al. . |
| 4,655,771 | 4/1987 | Wallsten ........................................ 623/1 |
| 4,921,484 | 5/1990 | Hillstead ................... 606/194 |
| 4,998,539 | 3/1991 | Delsanti ................... 606/194 |
| 5,002,560 | 3/1991 | Machold et al. . |
| 5,026,377 | 6/1991 | Burton et al. ............................ 606/108 |
| 5,034,001 | 7/1991 | Garrison et al. . |
| 5,053,014 | 10/1991 | Van Heugten ........................... 604/167 |
| 5,071,407 | 12/1991 | Termin et al. ........................... 606/194 |
| 5,180,368 | 1/1993 | Garrison et al. . |

FOREIGN PATENT DOCUMENTS 4786590  4/1991  Australia .

OTHER PUBLICATIONS

Search Report in corresponding European Application EP 92200294.4.

Primary Examiner—Debra S. Brittingham
Attorney, Agent, or Firm—Peter C. Richardson; Lawrence C. Akers; Philip C. Strassburger

[57] ABSTRACT

A catheter with a self-expanding stent of a permeable mesh of stiff intersecting fibers is provided. A tubular outer catheter shaft holds the stent under tension at its distal end and from which the stent can be released for placement. A displaceable inner catheter inside the tubular outer catheter shaft supports the stent axially at its proximal end. In order to release the stent, the outer catheter shaft is retracted with respect to the inner catheter. A process for producing this catheter is also described. The stent is secured by gripping it at its proximal end in such a way that it forms a permeable mesh cone that expands automatically together with the stent and has a radius that increases gradually to the radius of the relaxed stent. The stent is securely anchored on the inner catheter with the help of the mesh cone.

12 Claims, 3 Drawing Sheets

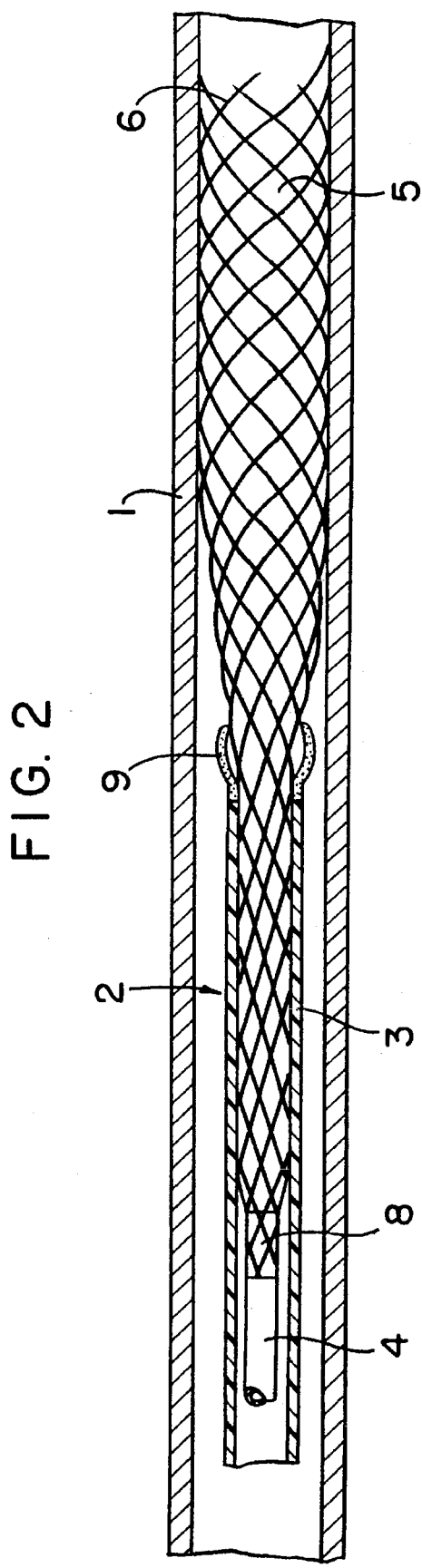

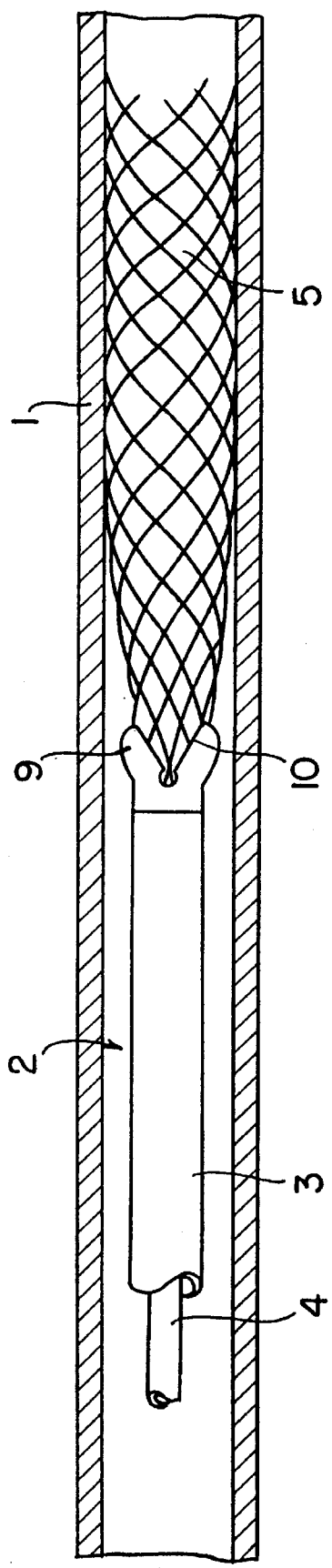

CATHETER WITH A STENT

This is a continuation of application Ser. No. 08/010,102 filed on Jan. 28, 1993, now abandoned.

BACKGROUND OF THE INVENTION

This invention concerns a catheter with a cylindrical stent of a permeable mesh of stiff intersecting fibers. When the stent is used it expands on its own due to its radial elasticity from a tense condition with a small circumference into a relaxed state supporting the vascular wall with a large circumference that is uniform over the length. A tubular outer catheter shaft holds the stent under tension at the distal end in such a way that the stent can be released from the catheter in order to be used. A displaceable internal catheter inside the tubular outer catheter shaft supports the stent axially at the proximal end thereof, whereby the outer catheter shaft is retracted with respect to the internal catheter in order to release the stent.

Such catheters are known, for example, from U.S. Pat. No. 4,655,771. They are used to position vascular supports, vascular endoprostheses or so-called stents in vessels in the human body. Recently, a special field of use for these stents has developed in conjunction with increased use of percutaneous transluminal coronary angioplasty (PTCA). In this technique, a catheter is inserted into a blood vessel through a puncture in the skin and is advanced through the blood vessel up to an arteriosclerotic occlusion in coronary vessels, for example. An inflatable balloon is attached to the end of the catheter. This balloon is inflated and the occlusion in the blood vessel is enlarged by this pressure. Then the balloon can be deflated again and the catheter removed from the body. In most cases, the blood vessel then remains open for continued blood flow.

One main complication of this technique, however, is that it causes detachment of parts of the intima, the innermost layer of the vascular wall, from the vascular wall so they then interfere with flow in the vessel to various extents. In the worst case the fragments of vascular wall released in this way can act like a valve to completely obstruct the flow passage. At certain locations, e.g., in the coronary arteries, such an occurrence can lead to a critical situation necessitating an emergency bypass operation which entails a high risk for the patient. However, even at other treatment sites and with a less unfavorable course of the complication, the desired result of the treatment is in any case hindered by this complication.

In the case of such complications, the stents known for some time, e.g., from U.S. Pat. No. 4,655,771, have been used at the treated site in the vessel to hold the vessel open from the inside. To do so, a catheter is inserted into the blood vessel through the same puncture already used for the balloon catheter. The stent is inside this catheter on the distal end relative to the user. The stent is cylindrical and consists of a network of stiff intersecting fibers. It is the self-expanding type, i.e., it is inserted into the catheter under tension and then relaxes on its own without assistance. Other types of stents must be converted to their expanded form by means of an interior balloon. At the treatment site the stent is released from the catheter by retracting the outside catheter and then detaching the stent from the catheter. A displaceable internal catheter inside the catheter serves as a support for the stent as long as the outside catheter is retracted. The stent remains in the vessel after being released and thus provides permanent support for the vessel. However, the catheter is retracted as usual and the puncture site in the vessel is sealed.

Such stents usually fulfill their purpose by pressing the intima, the innermost detached layer of the vessel, back against the vascular wall and thus they keep the vessel open for the flow of blood. However, problems occur since these stents can cause blood clots. This danger must be counteracted with high doses of anticoagulants which are also potentially dangerous. After a few weeks, the stent is then overgrown by the vascular intima, the endothelium, and the danger of blood clots is thus largely eliminated. But now a new problem has occurred. It has been found that the tissue cells whose growth is stimulated by the introduction of the stent cannot stop growing in some cases, so this results in a new partial or complete occlusion of the vessel.

At the same time, it is known that detached intima can become attached to the vascular wall again within a relatively short period of time and can heal there. In some cases renewed brief inflation of the balloon at the end of the aforementioned balloon catheter is sufficient to accomplish this. While the balloon is under pressure, the flow of blood in the respective vessel is interrupted, so this method cannot be used at all treatment sites. In addition, healing times are prolonged due to the need for anticoagulants during treatment.

In order to eliminate the problems described above, catheters have already been described where the stent is used to support the vessel wall only temporarily and then can be removed from the vessel again.

An example of this is given in European Patent 0 321 912 A1, which concerns a stent consisting of mesh tubing of woven wires that can be stretched longitudinally and inserted into the vessel. Then at the treatment site the two ends of the mesh tubing are advanced toward each other so the mesh bulges out between the two ends to form a hollow shape which presses against the inside wall of the vessel and thus supports it. The mesh of which this stent is made is thus not self-expanding but instead is stretched in its relaxed state. In this relaxed but stretched state with a small circumference, the stent is inserted into the vessel and removed from the vessel again after use. The pressure of the hollow form on the vascular wall varies according to how much the ends of the mesh tubing are advanced toward each other.

One disadvantage of this design, however, is that the individual wires can bend when the ends of the mesh tubing are pushed together too strongly and then the wires cannot yield in the vessel. Complications occur when removing a catheter with bent wires from a vessel because the actuating elements of the mesh can transmit compressive forces only to a limited extent in order to return the mesh to the elongated form with a small circumference. Another disadvantage is that the mesh is gathered at both ends so the blood flow must pass through the mesh twice when it is in position in the blood vessel, i.e., once at the proximal end of the stent and the second time at the distal end of the stent. Another disadvantage is that the actuating forces holding the mesh tubing open during the duration of the treatment must be maintained over a relatively great distance from the outside. This can result in transmission errors when, for example, the catheter is advanced between the point of puncture into the skin and the point of treatment.

Another example of a stent that can be removed from the body is disclosed in World Patent WO 91/07928 where the stent consists of a single wire coiled into a helical shape. The wire is stretched and accommodated in a thin catheter tube from which it is also advanced forward. As soon as the wire comes out of the thin catheter tube at the distal end, it assumes its spiral shape or helical shape again because of the stresses imprinted on it. The individual coils of the helical wire press radially outward and thus support the vascular wall. To remove this stent the wire is again retracted into the catheter. The wire then returns to its elongated form. This stent is thus the self-expanding type.

With the self-expanding type there is no danger of excessive operating forces having a negative effect on the stent or even rendering it useless. The flow conditions for blood are favorable with this type of stent, as can be imagined, because the helix is open at the distal end from the catheter and thus the blood must flow through the windings of the helix only once.

Use of just one wire, however, has the disadvantage that the wires of the stent must be very close together in order to effectively support a large area of vascular wall. In a helical form with just one wire, however, the windings do not hold together in such a way that would assure uniformly close spacing of the windings. This can result in gaps in the support provided for the vascular wall. Another unpleasant disadvantage is that the helical stent does not remain stationary on insertion and removal from the vessel. On insertion and removal of the stent, the relaxed portion of the helical spring must rotate with respect to the wire in the catheter in order to compensate for the difference in the condition of the wire. The freely rotating end of the wire can cause damage to the vascular wall when positioning the stent. However, the main disadvantage is that the rotation of the helical stent as it is being positioned can cause it to slip under a detached flap of vascular wall and thus prevent the stent from fulfilling its function. This stent is therefore definitely not as effective as the known stent that remains permanently in the vessel. In addition, the high frictional forces of the wire when it is under tension in the thin catheter also cause problems. Therefore, a great resistance must be overcome in order to expel the stent from the catheter, and this resistance may be further increased by the pressure of the wire against the catheter wall when it is being expelled.

Another example of a stent that can be removed from the vessel is disclosed in European Patent 0 423 916 A1. This is a slidable lattice grate in the form of a segment of tubular sheathing made of stainless steel wire. This stent is also the self-expanding type and is inserted into the vessel by retracting an outside catheter with respect to an inside catheter exactly like the stent according to U.S. Pat. No. 4,655,771. On the proximal edge of the slidable lattice grate that forms a segment of tubular sheathing, a thread is provided on the edge of the tubing. With this thread the tubing can be gathered at the proximal end. In order to accomplish this, both ends of the thread extend outside the body where they are secured loosely as long as the stent remains in the body. When the stent is to be removed, a new catheter is advanced as far as the stent by means of these two threads and the proximal end of the stent is tightened by pulling on these threads accordingly. Then a second larger catheter is advanced over the first. The stent is then gathered with these threads until it fits inside the larger catheter and can be inserted into it. Next, the two catheters together with the stent are removed.

One advantage of this arrangement is the good flow achieved when the stent is in place in the vessel because the segment of tubing is open at both ends. A disadvantage is the great effort required for this arrangement. The procedure is very tedious due to the handling of the threads and the need to insert at least one new catheter which also must be advanced into the proper position by means of the threads.

The instrumental expense is also very high because at least one additional catheter must also be provided to accommodate the stent again. The catheter used for insertion of the stent is too small for this purpose. When the stent is inserted into coronary arteries, problems can also be expected on insertion of the stent into the larger catheter because the coronary arteries are in constant motion. Problems therefore come about due to the fact that the stent, which is gathered together at the proximal end, is not always positioned exactly in the middle with respect to the larger catheter, nor is it automatically centered with respect to the larger catheter. Therefore, the stent remains stuck at the edge of the larger catheter.

SUMMARY OF THE INVENTION

The task of this invention is therefore to further develop a catheter with a stent that is held together on its own and does not twist when released, so the stent can be removed again reliably from the vessel with no problem after a temporary period of use. The stent that is to be improved upon by the present invention should be of the self-expanding type in order to assure a no-risk procedure with the removable stent. The catheter should have the simplest possible design and should be easy and simple to manipulate. The flow of medium during the temporary period of use of the stent in the vessel should be hindered as little as possible. At the same time, a process for producing this catheter is also to be developed.

This problem is solved by the fact that the stent is secured under tension at its proximal end in such a way that it forms a permeable mesh cone with the stent that expands automatically and the radius of the cone increases gradually to the radius of the relaxed stent. The stent is anchored securely on the inside catheter with the help of the mesh cone.

A catheter with a stent can thus be produced by these measures so that after it is used it can be removed reliably and with no problem from the vessel together with the stent. To accomplish this, the outer catheter shaft must be advanced with respect to the displaceable inside catheter, and when the stent has been detached from the vessel wall, the displaceable catheter may then optionally be retracted. Next, starting from the tip, the outer catheter shaft slides along the outside of the mesh cone anchored on the inside catheter and thus forces the stent and the mesh cone formed by the stent back into a form where it is under tension.

Due to the conical shape at the proximal end of the stent, the stent cannot become entangled and the stent centers itself with respect to the outer catheter shaft. Therefore, the outer catheter shaft can be advanced smoothly over the stent from the beginning and the stent can be retracted smoothly into the catheter. The contracting forces are large enough due to the shape of the mesh cone but are also distributed so uniformly that the stent can be returned to the original small circumference and will fit back into the same outer catheter shaft used originally. When the entire length of the stent is again accommodated inside the outer catheter shaft, the catheter can then be removed as a whole together with the stent.

Thus, these procedures not only result in a catheter with the simplest possible design without any new additional parts but also a catheter that can be manipulated easily and reliably. Essentially only frictional forces occur, known from the traditional permanently positioned stent, in addition to the low forces for contracting the stent. The elements of the procedure are as simple as possible and are also the same as the manipulations associated with the traditional permanent stent. At the same time, the stent is secured on the inside catheter due to the use of the permeable mesh cone as the means of attachment, so the flow of medium in the vessel is minimally hindered.

If the stent is contracted to the outside diameter of the inside catheter at the tip of the mesh cone and is connected to the inside catheter by a layer of binder, the result is a catheter that has an especially simple design, is simple to manufacture and has a smooth transition from the inside catheter to the tip of the mesh cone.

Another special embodiment is obtained when the inside catheter is designed as a tube and ends inside the stent. The tubular inside catheter can hold a guide wire, for example, so the stent can be advanced along a guide wire already in place in the body. If the inside catheter does not project distally out of the stent at the distal end, the catheter can also be used for a method of removing blood clots from arteries and veins with the help of a so-called Fogarty catheter as described in German Utility Patent 89 10 603.2 in addition to its use for insertion of a removable stent. For this purpose, the inside catheter does not have a guide wire in its lumen but instead holds a balloon catheter, i.e., the Fogarty catheter. This balloon catheter may then optionally be equipped with an inside guide wire.

In contrast with the balloons of the aforementioned balloon catheters, the balloon of this Fogarty catheter is elastic, i.e., it can largely adjust to the diameter of the vessel. The Fogarty catheter is advanced out of the inside catheter, through the blood vessel and through a blood clot in the blood vessel. The balloon of the Fogarty catheter is inflated behind the blood clot and the Fogarty catheter is retracted. The inflated balloon then pushes the clot in front of it in the blood vessel until the blood clot is trapped between the balloon and the catheter according to this invention.

In order to carry out the method according to German Utility Patent 89 10 603.2, the distal end of the stent must then be used as a trap. The stent is advanced until its distal end projects out of the outer catheter shaft and has widened to the diameter of the vessel. This forms a trap into which the blood clot can be inserted with the help of the Fogarty balloon at the distal end of the outer catheter shaft. The trap or the stent used as a trap is then retracted back into the outer catheter shaft of the catheter according to this invention. The trap then contracts again, squeezing the blood clot and separating the liquid components from the fibrous components. When the internal catheter together with the trap is retracted further, the stent that serves as a trap is accommodated again in the outer catheter shaft together with the fibrous components of the blood clot.

The blood clot can then be removed together with the catheter. For the method according to German Utility Patent 89 10 603.2 it was considered advantageous to cover the trap with an impervious coating or membrane so the blood clot could not escape from the trap. However, it has been found that the mesh, which becomes smaller in the direction of the catheter shaft with the stent of the catheter according to this invention, is sufficient to retain the fibrous components of the blood clot and therefore the catheter according to this invention can also be used for the method according to German Utility Patent 89 10 603.2. This measure thus yields a multipurpose instrument that can be used as a removable stent or as a device for removing blood clots from arteries and veins.

The outer catheter shaft of the multipurpose instrument described above can also be provided with a safety cap that can be punctured by the stent. The catheter is then no longer entirely open at the front when advanced through the vessel. This mainly prevents injury to the vascular wall by the distal edge of the outer catheter shaft. Despite this protection in advancing the stent, the stent can still be released at the site of treatment because it can puncture the safety cap.

An especially advantageous method of producing a catheter according to this invention is obtained when the tip of the mesh cone of the stent is held on the outside diameter of the inside catheter by a heat-shrink tube while the mesh cone is connected to the inside catheter. Thus by a simple measure the mesh of the stent is uniformly gripped on all sides and the connection can be established easily by means of a heat treatment or with the help of binders. One particular advantage of this method is that the gripping exerts a constant force even when the object gripped is yielding or even undergoes a reduction in diameter. This unique aspect of the proposed process is important when the connection is created by means of a heat treatment but also when the smallest possible diameter of the finished connection is to be achieved when using binders.

BRIEF DESCRIPTION OF THE DRAWINGS

This invention will now be described in greater detail on the basis of a practical example as illustrated in the figures which show the following:

FIG. 2 shows a cross section through a catheter according to this invention with the stent partially secured and partially released.

FIG. 3 shows a view of a catheter according to this invention with the stent partially released.

DETAILED DESCRIPTION OF THE INVENTION

Figure 1:
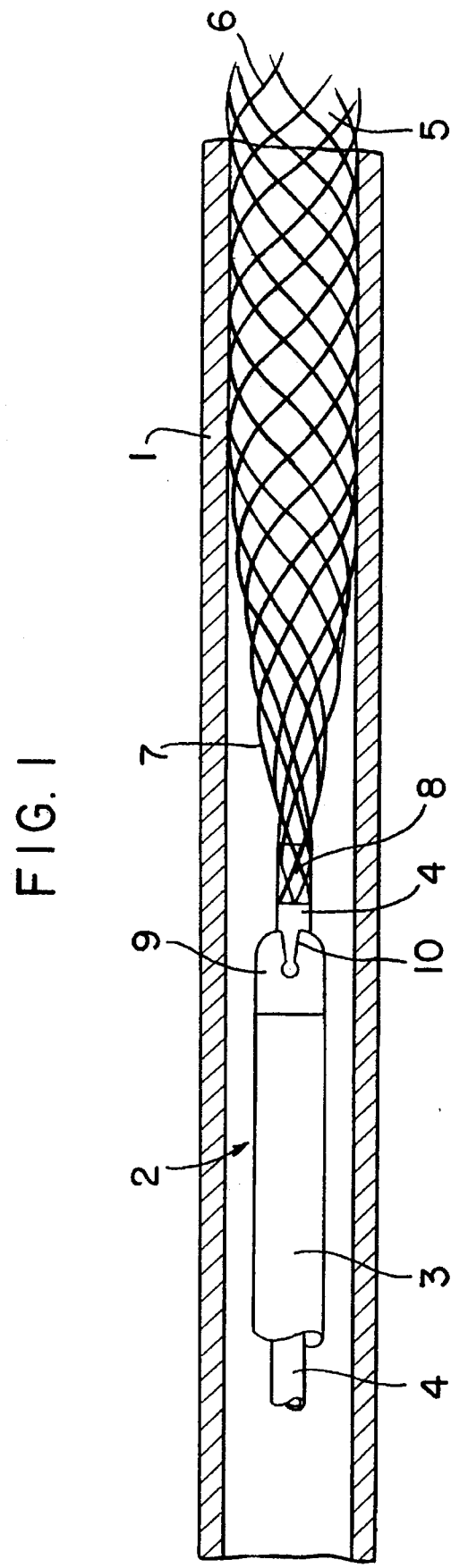
FIG. 1 shows a view of a catheter according to this invention with the stent released in a vessel indicated schematically.

FIG. 1 shows an idealized vessel 1 in a human body, for example. The vessel may hold fluids such as blood, but it may also carry air, so the vessel may also be a trachea. The distal end of a catheter 2 on the opposite end from the person manipulating it is inside this vessel. Catheter 2 has been inserted into this vessel at a suitable location, e.g., at a puncture, and advanced from outside the body to the point in the vessel illustrated here. Catheter 2 consists of a tubular outer catheter shaft 3 and a displaceable inside catheter 4 accommodated in the former. In the position shown in FIG. 1, the inside catheter 4 has been advanced a certain distance out of the distal end of the outer catheter shaft 3.

In addition to catheter 2, there is also a stent 5 in vessel 1. Stent 5 is made of a permeable mesh of stiff intersecting fibers 6. The stiffness of fibers 6 is selected so that stent 5 will expand on its own due to its radial elasticity from a condition under tension with a small circumference into a relaxed state where it supports the vascular wall with a uniform circumference over its length.

FIG. 2 shows a part of stent 5 under tension. In the left half of the figure, the tense part of stent 5 is contracted to a small circumference at the distal end and accommodated in the tubular outer catheter shaft 3. The outer catheter shaft 3 must be retracted with respect to inside catheter 4 in order to release stent 5 for placement in its relaxed state where it expands automatically, pressing against the vascular wall and thus supporting it. The inside catheter 4 must provide axial support for the proximal end of the stent 5 in contact with the inside wall in the outer catheter shaft 3 to permit a relative movement between the outer catheter shaft 3 and the stent 5.

At its distal end stent 5 is open so the medium can flow freely through vessel 1. However, it can be seen especially in FIG. 1 that the stent is secured by clamping at its proximal end near the operating end in such a way that it forms a permeable mesh cone 7. Mesh cone 7 is made of the same stiff fibers 6 as stent 5, so it opens automatically together with the stent. The radius of this mesh cone 7 increases slowly to the radius of stent 5. At its tip, mesh cone 7 is contracted to the outside diameter of the inside catheter 4. It is connected there to the inside catheter by a layer of binder. Stent 5 is therefore anchored securely to inside catheter 4 with the help of mesh cone 7 at connection point 8.

An advantageous method of producing a catheter 2 according to this invention consists of holding stent 5 on the outside diameter of the inside catheter 4 at the proximal end with heat-shrink tubing, while the mesh cone 7 is connected to the inside catheter 4. In its starting form when it still has a large diameter, the heat-shrink tubing is pulled over stent 5. The heat-shrink tubing is then heated so it contracts and thus also constricts the stent 5 which it surrounds. The dimensions and material of the heat-shrink tubing as well as the supply of heat to the heat-shrink tubing can be selected so that the heat-shrink tubing contracts stent 5 onto the outside diameter of inside catheter 4 and holds it there. In this form, stent 5 can then be welded to inside catheter 4, or as an alternative, a layer of binder that was introduced previously or migrates into connection 8 through capillary action under the heat-shrink tubing can harden to form the bond. After this process, the heat-shrink tubing can be removed again, leaving a smooth connection 8 as shown in FIGS. 1 and 2 that can have essentially the diameter of inside catheter 4, depending on the method selected.

To use stent 5, it is first accommodated in catheter 2 under tension at the distal end inside the outer catheter shaft 3. Inside catheter 4 is retracted with respect to outer catheter shaft 3 and stent 5 is in contact with the wall of the outer catheter shaft 3, as shown in the left part of FIG. 2. The inside catheter is retracted to the extent that the distal end of stent 5 is inside the outer catheter shaft 3. In this condition, catheter 2 is inserted into vessel 1 and advanced in this vessel 1. When the distal end of catheter 2 has passed the point of treatment, the outer catheter shaft is retracted with respect to inside catheter 4 which is held stationary. Due to the connection of stent 5 with the stationary inside catheter 4, there is a relative movement between the stent and the outer catheter shaft 3. Therefore, stent 5 is gradually released, starting from its distal end. It comes out at the distal end of outer catheter shaft 3 and slowly expands in its relaxed state so it is in contact with the vascular wall and supports it. FIG. 2 shows the condition when the outer catheter shaft 3 is retracted for approximately half its length. The stent is then released as far as necessary, e.g., until connection 8 has come out of the distal end of outer catheter shaft 3 as shown in FIG. 1.

If stent 5 should then be removed again from vessel 1, the outer catheter shaft 3 must simply be advanced again with respect to inside catheter 4. Due to the connection of stent 5 to inside catheter 4, this also yields a relative movement between stent 5 and outer catheter shaft 3. Due to the connection of stent 5 to inside catheter 4 with the help of mesh cone 7 whose tip is attached to inside catheter 4, the outer catheter shaft 3 slides on the outside of the mesh of stent 5 and thus forces the mesh cone 7 rising out of the inside catheter 4 together with stent 5 connected to it back into its taut form in which it can be accommodated again in catheter shaft 3. As soon as the stent has separated from the vascular wall, the inside catheter 4 can also be retracted with respect to outer catheter shaft 3. In this way, stent 5 can be retracted again completely back into outer catheter shaft 3 and catheter 2 can be removed from vessel 1.

In the embodiment shown here, the inside catheter 4 is also designed as a length of tubing and the inside catheter 4 ends distally after connection 8. When in use, tubular inside catheter 4 holds a guide wire, for example. This may be a guide wire that is advanced for insertion of catheter 2 in the body so catheter 2 can follow the guide wire. However, it may also be a guide wire that is already inside the body from a previous treatment, e.g., from a treatment with a balloon catheter.

It can be seen in FIGS. 1 and 2 that the inside catheter 4 ends immediately after connection 8. Catheter 2 can in this case also be used for a process previously described for removing blood clots from arteries and veins according to German Utility Patent 89 10 603.2 in addition to its use for insertion of a removable stent 5. This method is described in detail above as well as in the source cited above, so the description will not be repeated here. In order to be able to use catheter 2 as a multipurpose instrument, inside catheter 4 need not end directly after connection 8, but may also end at a distance from the distal end of stent 5. It is sufficient for the inside catheter to end inside of stent 5 in any case.

A safety cap 9 is provided on the distal end of outer catheter shaft 3. It is thermally bonded to catheter shaft 3 or bonded with binders, but it can also be molded in one piece from the same material as catheter shaft 3. Safety cap 9 can be shaped elastically or permanently. This safety cap 9 is closed when catheter 2 is inserted into vessel 1. It thus prevents excessive penetration of fluid from the vessel into catheter 2. Cap 9 has a rounded tip. Due to the cover on the distal edge of the outer catheter shaft 3, the rounded tip and its flexibility, cap 9 prevents damage to the vascular wall when catheter 2 is being advanced in the vessel.

When catheter 2 has reached the location for treatment, cap 9 is punctured by stent 5 which is advanced relative to the outer catheter shaft 3 and thus the cap is opened. Slits 10 in cap 9 can facilitate this process. FIG. 3 shows cap 9 in the fully expanded condition and FIG. 2 shows cap 9, which is elastic in this case, partially closed again because the diameter of inside catheter 4 is smaller than the largest diameter.

When stent 5 has been retracted again entirely into the outer catheter shaft 3, cap 9 closes again if it is an elastic cap 9. Since there is no longer any danger of damage to the vascular wall due to the edge of catheter shaft 3 in retraction of catheter 2 out of vessel 1, cap 9 can be designed so that it does not close automatically after use of stent 5, but instead cap 9 may remain in the position assumed last.

We claim:

1. A catheter comprising:
   (a) a tubular outer catheter having a distal end and an elastic safety cap attached to the distal end;
   (b) an inner catheter having a proximal portion and a distal portion, the inner catheter disposed at least in part within the outer catheter and axially movable relative to the outer catheter; and
   (c) a permeable mesh self-expanding stent having a proximal portion and a distal portion, the proximal portion of the stent overlapping and attached to the distal portion of the inner catheter in an overlapping portion, the overlapping portion having an outer diameter defined by the diameter of the proximal portion of the stent, wherein said elastic safety cap is adapted to close upon withdrawal of the stent.

2. The catheter of claim 1 wherein the proximal portion of the stent has an outer diameter and the diameter of the overlapping portion does not exceed the outer diameter of the stent proximal portion.

3. The catheter of claim 1 wherein the stent forms a mesh cone gradually increasing in diameter between the proximal portion of the stent and the distal portion of the stent, the distal portion of the stent adapted to self-expand upon deployment from the outer catheter to make contact with a vessel wall.

4. The catheter according to claim 1 wherein the permeable mesh self-expanding stent is connected to the inner catheter by a binder.

5. The catheter according to claim 4 wherein the stent is connected to the inner catheter only by a binder.

6. The catheter according to claim 1 wherein said inner catheter is a tube with a distal portion that ends inside the permeable mesh self-expanding stent.

7. The catheter according to claim 1 wherein the safety cap is adapted to be penetrated by the permeable mesh self-expanding stent.

8. A catheter comprising:
   (a) a tubular outer catheter having a proximal portion and a distal portion;
   (b) an elastic safety cap affixed to the distal portion of the outer catheter;
   (c) an inner catheter disposed at least in part within the outer catheter; and
   (d) a permeable mesh self-expanding stent having a proximal end and a distal end, the stent attached to the distal portion of the inner catheter;
wherein the inner tube is adapted for axial movement within the outer catheter to carry the stent in a distal direction to penetrate the safety cap thereby allowing further distal movement of the stent, wherein said elastic safety cap is adapted to close upon withdrawal of the stent.

9. The catheter of claim 8 wherein the proximal portion of the stent is attached to the distal portion of the inner catheter to form a mesh cone gradually increasing in diameter between the proximal portion of the stent and the distal portion of the stent.

10. The catheter of claim 8 wherein the safety cap contains apertures to facilitate the penetration thereof.

11. The catheter according to claim 8 wherein said inner catheter is a tube with a distal portion that ends inside the permeable mesh self-expanding stent.

12. A method for deploying a stent with a catheter comprising a tubular outer catheter having a proximal portion and a distal portion; an elastic safety cap affixed to the distal portion of the outer catheter; an inner catheter disposed at least in part within the outer catheter; and a permeable mesh self-expanding stent having a proximal end and a distal end, the stent attached to the distal portion of the inner catheter; wherein the inner tube is adapted for axial movement within the outer catheter to carry the stent in a distal direction to penetrate the safety cap thereby allowing further distal movement of the stent; the method comprising:
   a) advancing the catheter to a treatment site within a body vessel;
   b) moving the tubular outer catheter proximally relative to the inner catheter so that the distal end of the stent penetrates the safety cap to deploy at least part of the stent outside of the outer tube;
   c) allowing at least the distal portion of the stent to self-expand and make contact with a body vessel; and then
   d) moving the outer tubular catheter distally relative to the inner catheter to withdraw the stent into the outer tube and allowing the elastic safety cap to close.

* * * * *